US007890176B2

(12) United States Patent
Jaax et al.

(10) Patent No.: US 7,890,176 B2
(45) Date of Patent: Feb. 15, 2011

(54) METHODS AND SYSTEMS FOR TREATING CHRONIC PELVIC PAIN

(75) Inventors: Kristen N. Jaax, Saugus, CA (US); Rafael Carbunaru, Studio City, CA (US); Todd K. Whitehurst, Santa Clarita, CA (US); Carla Mann Woods, Beverly Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1510 days.

(21) Appl. No.: 11/156,360

(22) Filed: Jun. 17, 2005

(65) Prior Publication Data

US 2005/0228451 A1    Oct. 13, 2005

Related U.S. Application Data

(63) Continuation-in-part of application No. 09/931,804, filed on Aug. 16, 2001, now Pat. No. 6,941,171, which is a continuation-in-part of application No. 09/642,979, filed on Aug. 18, 2000, now Pat. No. 6,735,474, which is a continuation-in-part of application No. PCT/US99/14775, filed on Jun. 29, 1999.

(60) Provisional application No. 60/091,762, filed on Jul. 6, 1998, provisional application No. 60/173,054, filed on Dec. 24, 1999.

(51) Int. Cl.
*A61N 1/00* (2006.01)

(52) U.S. Cl. ...................................................... 607/39
(58) Field of Classification Search ................. 607/1–2, 607/39, 115–118, 138
See application file for complete search history.

(56) References Cited

U.S. PATENT DOCUMENTS 3,157,181 A    11/1964   McCarty
3,403,684 A    10/1968   Ariel et al.

(Continued)

FOREIGN PATENT DOCUMENTS

EP           245547 B1    8/1990

(Continued)

OTHER PUBLICATIONS

Reid et al. "Day-case herniotomy in children. A comparison of ilio-inguinal nerve block and wound infiltration for postoperative analgesia." Anaesthesia. Jun. 1987; 42(6):658-61.*

*Primary Examiner*—Mark W Bockelman
*Assistant Examiner*—Elizabeth K So
(74) *Attorney, Agent, or Firm*—Wong, Cabello, Lutsch, Rutherford & Brucculeri, LLP

(57) ABSTRACT

Methods of treating chronic pelvic pain include applying at least one stimulus to a stimulation site within a patient with an implanted system control unit in accordance with one or more stimulation parameters. Systems for treating chronic pelvic pain include a system control unit configured to apply at least one stimulus to a stimulation site within a patient in accordance with one or more stimulation parameters.

14 Claims, 10 Drawing Sheets

U.S. PATENT DOCUMENTS

| | | |
|---|---|---|
| 3,650,276 A | 3/1972 | Burghele et al. |
| 3,667,477 A | 6/1972 | Susset et al. |
| 3,760,984 A | 9/1973 | Theeuwes |
| 3,845,770 A | 11/1974 | Theeuwes et al. |
| 3,870,051 A | 3/1975 | Brindley |
| 3,916,899 A | 11/1975 | Theeuwes et al. |
| 3,923,426 A | 12/1975 | Theeuwes et al. |
| 3,941,136 A | 3/1976 | Bucalo |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,157,087 A | 6/1979 | Miller et al. |
| 4,165,750 A | 8/1979 | Aleev et al. |
| 4,203,440 A | 5/1980 | Theeuwes |
| 4,203,442 A | 5/1980 | Michaels |
| 4,210,139 A | 7/1980 | Higuchi |
| 4,279,256 A | 7/1981 | Bucalo |
| 4,327,725 A | 5/1982 | Cortese et al. |
| 4,360,019 A | 11/1982 | Portner et al. |
| 4,387,719 A | 6/1983 | Plevnik et al. |
| 4,390,023 A | 6/1983 | Rise |
| 4,406,288 A | 9/1983 | Horwinski et al. |
| 4,487,603 A | 12/1984 | Harris |
| 4,537,195 A | 8/1985 | McDonnell |
| 4,559,951 A | 12/1985 | Dahl et al. |
| 4,562,751 A | 1/1986 | Nason et al. |
| 4,569,351 A | 2/1986 | Tang |
| 4,607,639 A | 8/1986 | Tanagho et al. |
| 4,612,934 A | 9/1986 | Borkan |
| 4,627,850 A | 12/1986 | Deters et al. |
| 4,628,934 A | 12/1986 | Pohndorf et al. |
| 4,678,408 A | 7/1987 | Nason et al. |
| 4,685,903 A | 8/1987 | Cable et al. |
| 4,692,147 A | 9/1987 | Duggan |
| 4,703,755 A | 11/1987 | Tanagho et al. |
| 4,725,852 A | 2/1988 | Gamblin et al. |
| 4,739,764 A | 4/1988 | Lue et al. |
| 4,771,779 A | 9/1988 | Tanagho et al. |
| 4,969,463 A | 11/1990 | Dahl et al. |
| 5,057,318 A | 10/1991 | Magruder et al. |
| 5,059,423 A | 10/1991 | Magruder et al. |
| 5,080,653 A | 1/1992 | Voss et al. |
| 5,094,242 A | 3/1992 | Gleason et al. |
| 5,097,122 A | 3/1992 | Colman et al. |
| 5,112,614 A | 5/1992 | Magruder et al. |
| 5,133,354 A | 7/1992 | Kallok |
| 5,137,727 A | 8/1992 | Eckenhoff |
| 5,193,539 A | 3/1993 | Schulman et al. |
| 5,193,540 A | 3/1993 | Schulman et al. |
| 5,199,430 A | 4/1993 | Fang et al. |
| 5,234,692 A | 8/1993 | Magruder et al. |
| 5,234,693 A | 8/1993 | Magruder et al. |
| 5,281,219 A | 1/1994 | Kallok |
| 5,300,094 A | 4/1994 | Kallok et al. |
| 5,312,439 A | 5/1994 | Loeb |
| 5,484,445 A | 1/1996 | Knuth |
| 5,486,160 A | 1/1996 | Rossi et al. |
| 5,501,703 A * | 3/1996 | Holsheimer et al. ............ 607/46 |
| 5,562,717 A | 10/1996 | Tippey et al. |
| 5,702,428 A | 12/1997 | Tippey et al. |
| 5,728,396 A | 3/1998 | Peery et al. |
| 5,755,750 A * | 5/1998 | Petruska et al. ................ 607/75 |
| 5,957,965 A | 9/1999 | Moumane et al. |
| 5,984,854 A | 11/1999 | Ishikawa et al. |
| 6,002,964 A * | 12/1999 | Feler et al. ..................... 607/46 |
| 6,051,017 A | 4/2000 | Loeb et al. |
| 6,055,456 A | 4/2000 | Gerber |
| 6,061,596 A | 5/2000 | Richmond et al. |
| 6,104,960 A | 8/2000 | Duysens et al. |
| 6,164,284 A | 12/2000 | Schulman et al. |
| 6,185,452 B1 | 2/2001 | Schulman et al. |
| 6,208,894 B1 | 3/2001 | Schulman et al. |
| 6,280,873 B1 | 8/2001 | Tsukamoto |
| 6,319,241 B1 * | 11/2001 | King et al. ..................... 604/502 |
| 6,360,750 B1 | 3/2002 | Gerber et al. |
| 6,368,315 B1 | 4/2002 | Gillis et al. |
| 6,381,496 B1 | 4/2002 | Meadows et al. |
| 6,393,323 B1 | 5/2002 | Sawan et al. |
| 6,430,442 B1 | 8/2002 | Peters et al. |
| 6,434,431 B1 | 8/2002 | Camps et al. |
| 6,458,171 B1 | 10/2002 | Tsukamoto |
| 6,512,958 B1 | 1/2003 | Swoyer et al. |
| 6,539,263 B1 | 3/2003 | Schiff et al. |
| 6,587,728 B2 | 7/2003 | Fang et al. |
| 6,620,151 B2 | 9/2003 | Blischak et al. |
| 6,662,052 B1 | 12/2003 | Sarwal et al. |
| 6,666,845 B2 | 12/2003 | Hooper et al. |
| 6,671,544 B2 | 12/2003 | Baudino |
| 6,712,772 B2 | 3/2004 | Cohen et al. |
| 6,735,474 B1 | 5/2004 | Loeb et al. |
| 6,740,072 B2 | 5/2004 | Starkweather et al. |
| 6,760,626 B1 | 7/2004 | Boveja |
| 6,770,067 B2 | 8/2004 | Lorenzen et al. |
| 6,847,849 B2 | 1/2005 | Mamo et al. |
| 7,013,177 B1 * | 3/2006 | Whitehurst et al. ............ 607/46 |
| 2001/0002441 A1 | 5/2001 | Boveja |
| 2001/0025192 A1 | 9/2001 | Gerber et al. |
| 2001/0046625 A1 | 11/2001 | Ruth, II et al. |
| 2001/0053476 A1 | 12/2001 | Ruth et al. |
| 2002/0055761 A1 | 5/2002 | Mann et al. |
| 2002/0111659 A1 | 8/2002 | Davis et al. |
| 2002/0147485 A1 | 10/2002 | Mamo et al. |
| 2002/0183802 A1 | 12/2002 | Fang et al. |
| 2002/0193840 A1 | 12/2002 | Sawan et al. |
| 2003/0004553 A1 | 1/2003 | Grill et al. |
| 2003/0014080 A1 | 1/2003 | Baudino |
| 2003/0018365 A1 | 1/2003 | Loeb |
| 2003/0028232 A1 | 2/2003 | Camps et al. |
| 2003/0045919 A1 | 3/2003 | Swoyer et al. |
| 2003/0100839 A1 | 5/2003 | Cohen et al. |
| 2003/0100930 A1 | 5/2003 | Cohen et al. |
| 2003/0139782 A1 | 7/2003 | Duncan et al. |
| 2003/0144710 A1 | 7/2003 | Haugland et al. |
| 2003/0191152 A1 | 10/2003 | Cutler |
| 2003/0208247 A1 | 11/2003 | Spinelli et al. |
| 2003/0236557 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0049240 A1 | 3/2004 | Gerber et al. |
| 2004/0059392 A1 | 3/2004 | Parramon et al. |
| 2004/0078070 A1 | 4/2004 | Baudino |
| 2004/0093053 A1 | 5/2004 | Gerber et al. |
| 2004/0093093 A1 | 5/2004 | Andrews |
| 2004/0102760 A1 * | 5/2004 | Hsue et al. .................... 604/512 |
| 2004/0111126 A1 | 6/2004 | Tanagho et al. |
| 2004/0152999 A1 | 8/2004 | Cohen et al. |
| 2004/0162594 A1 | 8/2004 | King |
| 2004/0193228 A1 | 9/2004 | Gerber |
| 2004/0215068 A1 | 10/2004 | Lykke et al. |
| 2004/0215287 A1 | 10/2004 | Swoyer et al. |
| 2005/0010259 A1 | 1/2005 | Gerber |
| 2005/0010260 A1 | 1/2005 | Gerber |
| 2005/0015117 A1 | 1/2005 | Gerber |
| 2005/0020970 A1 | 1/2005 | Gerber |
| 2005/0021008 A1 | 1/2005 | Gerber |
| 2005/0033372 A1 | 2/2005 | Gerber |
| 2005/0033373 A1 | 2/2005 | Gerber |
| 2005/0033374 A1 | 2/2005 | Gerber |

| | | | | |
|---|---|---|---|---|
| 2006/0195154 A1 * | 8/2006 | Jaax et al. .................. 607/45 | WO | WO 01/52729 A2 7/2001 |
| | | | WO | WO 01/54767 A1 8/2001 |
| FOREIGN PATENT DOCUMENTS | | | WO | WO 01/60445 A2 8/2001 |
| | | | WO | WO 01/82398 A1 11/2001 |
| EP | 780139 A1 | 6/1997 | WO | WO 02/20086 A1 3/2002 |
| EP | 1392393 B1 | 11/2004 | WO | WO 02/052703 A2 8/2002 |
| WO | WO 82/01656 A1 | 5/1982 | WO | WO 02/078592 A2 10/2002 |
| WO | WO 95/16424 A1 | 6/1995 | WO | WO 02/092165 A1 11/2002 |
| WO | WO 97/18857 A1 | 5/1997 | WO | WO 03/005465 A1 1/2003 |
| WO | WO 98/37926 * | 2/1998 | WO | WO 03/018113 A1 3/2003 |
| WO | WO 00/15293 A1 | 3/2000 | WO | WO 03/094693 A2 11/2003 |
| WO | WO 00/19939 A1 | 4/2000 | WO | WO 2004/047914 A1 6/2004 |
| WO | WO 00/25859 A1 | 5/2000 | | |
| WO | WO 00/01320 A3 | 6/2000 | * cited by examiner | |

# METHODS AND SYSTEMS FOR TREATING CHRONIC PELVIC PAIN

RELATED APPLICATIONS

The present application is a continuation-in-part application of U.S. application Ser. No. 09/931,804, filed Aug. 16, 2001, now issued as U.S. Pat. No. 6,941,171 which application is a continuation-in-part of U.S. patent application Ser. No. 09/642,979, filed Aug. 18, 2000, now issued as U.S. Pat. No. 6,735,474 which in turn is a continuation-in-part of PCT Patent Application Serial No. PCT/US99/14775, filed Jun. 29, 1999, which in turn claims the benefit of prior U.S. Patent Application Ser. No. 60/091,762, filed Jul. 6, 1998. U.S. patent application Ser. No. 09/642,979 also claims the benefit of U.S. patent application Ser. No. 60/173,054, filed Dec. 24, 1999. The above-listed applications are incorporated herein by reference in their entireties.

BACKGROUND

Chronic Pelvic Pain (CPP) is one of the most common medical problems affecting women today. Chronic pelvic pain occurs in the pelvic and/or abdominal region (e.g., beneath the umbilicus) and can last for up to six months or longer. Although men may also suffer from CPP, the majority of CPP patients are women. The prevalence of CPP among adult female populations in the United States and in the United Kingdom is estimated to be between fifteen and thirty-eight percent.

Diagnosis and treatment of CPP accounts for ten percent of all out-patient gynecologic visits, twenty percent of laparoscopies, and twelve to sixteen percent of hysterectomies at a cost of $2.8 billion annually in the United States. In spite of these invasive efforts, however, 1.5 million CPP patients in the United States alone remain refractory to treatment.

The personal cost to those suffering from CPP is even greater, affecting all aspects of their lives. About twenty-five percent of patients who suffer from CPP are bedridden for much of the day. Fifty-eight percent of CPP patients are forced to cut down on their usual activity one or more days per month. Almost ninety percent of CPP patients suffer pain during sexual intercourse. Many patients who suffer from CPP also experience sleep disturbance, constipation, diminished appetite, retarded body movements and reactions, emotional distress, and depression.

Chronic pelvic pain may be caused by a number of different disorders or injuries. For example, gynecologic conditions account for approximately ninety percent of all cases of CPP. Gastrointestinal diseases, such as irritable bowel syndrome, are the next most common diagnostic category. CPP may also be caused by systemic disorders and problems relating to a specific organ system, such as the urinary tract.

Endometriosis is the most common etiology of CPP in populations with a low prevalence of sexually transmitted diseases. By comparison, chronic pelvic inflammatory disease (PID) is one of the most common gynecologic conditions causing CPP in populations that do have a high prevalence of sexually transmitted diseases.

Although any one disorder may be the cause of CPP, CPP may also be caused by a combination of disorders. In some patients, the etiology of CPP cannot be determined. The absence of a clear diagnosis of CPP can frustrate both patients and clinicians.

Patients with CPP often have coexisting disorders or problems such as somatization disorders, drug and narcotic dependency, physical and sexual abuse experiences, mental health problems, and depression. For example, studies have shown that up to seventy percent of women with CPP have a coexisting somatization disorder. Patients with multiple physical complaints not fully explained by a known general medical condition may be given the diagnosis of somatization disorder. The *American Psychiatric Association's Diagnostic and Statistical Manual of Mental Disorders* (4th edition) criteria for this diagnosis requires the presence of at least four different sites of pain, two gastrointestinal symptoms other than pain, one neurological symptom, and one sexual or reproductive problem other than pain.

As mentioned, CPP is often accompanied by drug dependency. For example, many women with CPP consume narcotics on a regular basis. In addition, some women with CPP have underlying neuropsychiatric problems (e.g., an enhanced sensitivity to pain stimuli) that place them at risk for addiction. Hence, CPP may be remedied in part by discontinuing the consumption of narcotic analgesics and replacing them with pain medications that have a low abuse potential (e.g., low dosages of tramadol).

Studies have also shown that up to twenty-five percent of women with CPP have a history of physical and sexual abuse. These traumatic experiences can alter neuropsychological processing of pain signals and can permanently alter pituitary-adrenal and autonomic responses to stress. Such alterations of the neuropsychological processing of pain signals may instigate and/or promote CPP.

One common type of CPP is interstitial cystitis. Interstitial cystitis is characterized by urinary urgency, bladder discomfort, and a sense of inadequate emptying of the bladder. Dyspareunia is often present. Some women with interstitial cystitis experience pain in the lower abdomen. Pain associated with interstitial cystitis may be due to abnormal bladder epithelial permeability. Optimal treatment of interstitial cystitis is unclear.

Patients with CPP currently have very few treatment alternatives. CPP is often poorly controlled by medication. Surgery is often ineffective, as the pain may persist even after surgery. CPP may also be controlled through the use of a transcutaneous electrical nerve stimulation (TENS) system which masks local pain sensations with a fine tingling sensation. However, TENS devices can produce significant discomfort and can only be used intermittently.

SUMMARY

Methods of treating chronic pelvic pain include applying at least one stimulus to a stimulation site within a patient with an implanted system control unit in accordance with one or more stimulation parameters.

Systems for treating chronic pelvic pain include a system control unit configured to apply at least one stimulus to a stimulation site within a patient in accordance with one or more stimulation parameters.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for treating chronic pelvic pain (CPP) are described herein. An implanted system control unit is configured to apply at least one stimulus to a stimulation site within a patient in accordance with one or more stimulation parameters. The stimulus is configured to treat CPP and may include electrical stimulation, drug stimulation, chemical stimulation, thermal stimulation, electromagnetic stimulation, mechanical stimulation, and/or any other suitable stimulation.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
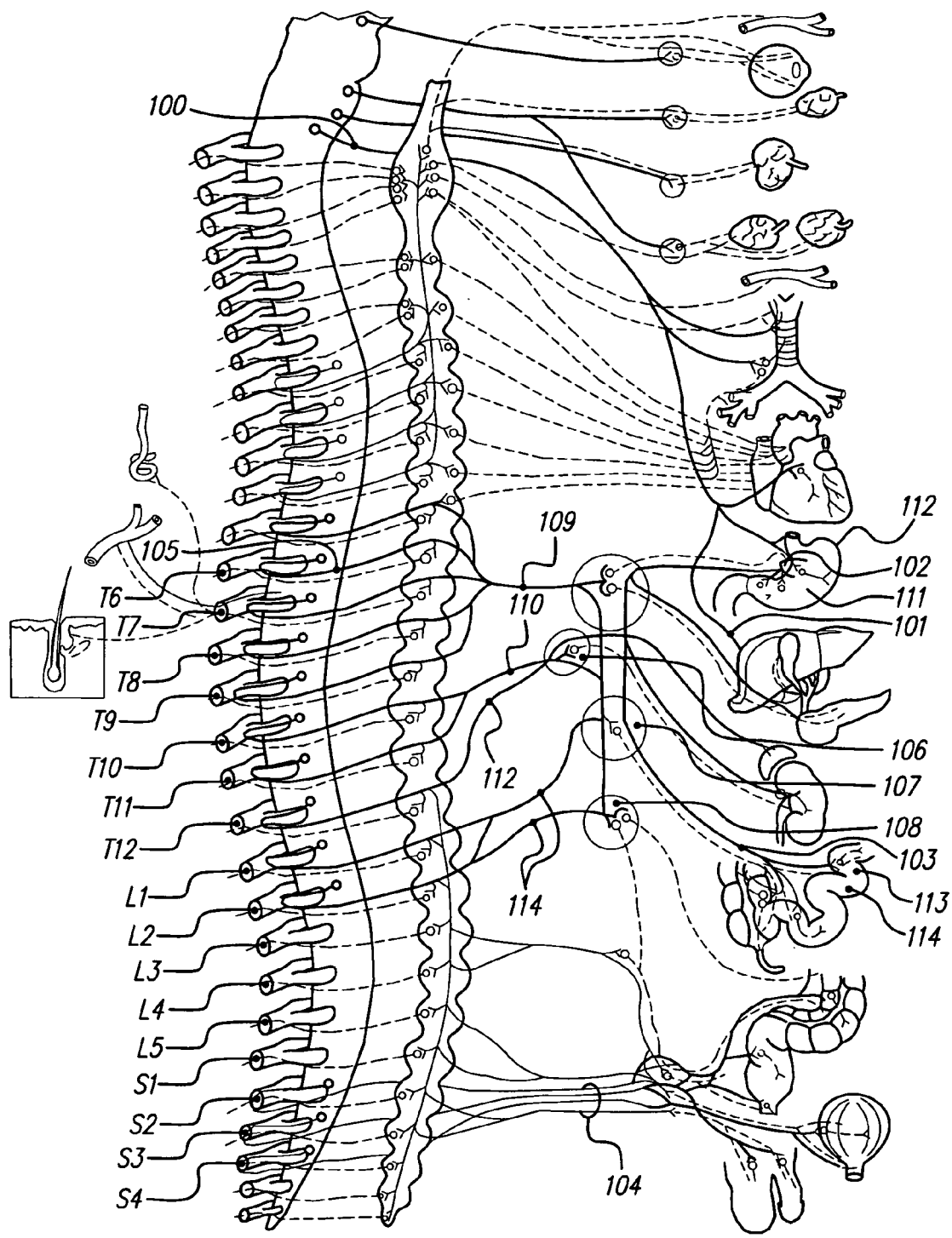
FIG. 1A is a schematic representation of the autonomic nervous system.

FIG. 1A is a schematic of the autonomic nervous system, including the parasympathetic nervous system and the sympathetic nervous system. FIG. 1A shows the following structures of the parasympathetic nervous system: the anterior or posterior vagus nerves (100), the hepatic branch (101) of the vagus nerve, the celiac branch (102) of the vagus nerve, the gastric branch (103) of the vague nerve, and branches of the pelvic plexus (104). FIG. 1A also shows the following structures of the sympathetic nervous system: the sympathetic afferent fibers (105) that exit the spinal cord at spinal levels T6, T7, T8, and T9, the sympathetic ganglia (e.g., the celiac (106) ganglia and its subsidiary plexuses, the superior mesenteric ganglia (107), and the inferior mesenteric ganglia (108), the greater splanchnic nerve (109) and the lesser splanchnic nerve (110). FIG. 1A also shows the smooth muscle (111) and high greater curvature (112) of the stomach and the enteric system including Meissner's plexus (113) and Auerback's plexus (114) of the stomach/intestines. Thoracic segments T10, T11, and T12; lumbar segments L1, L2, L3, L4, and L5; and sacral segments S1, S2, S3 and S4 of the spinal cord are also illustrated schematically in FIG. 1A.

Figure 1B:
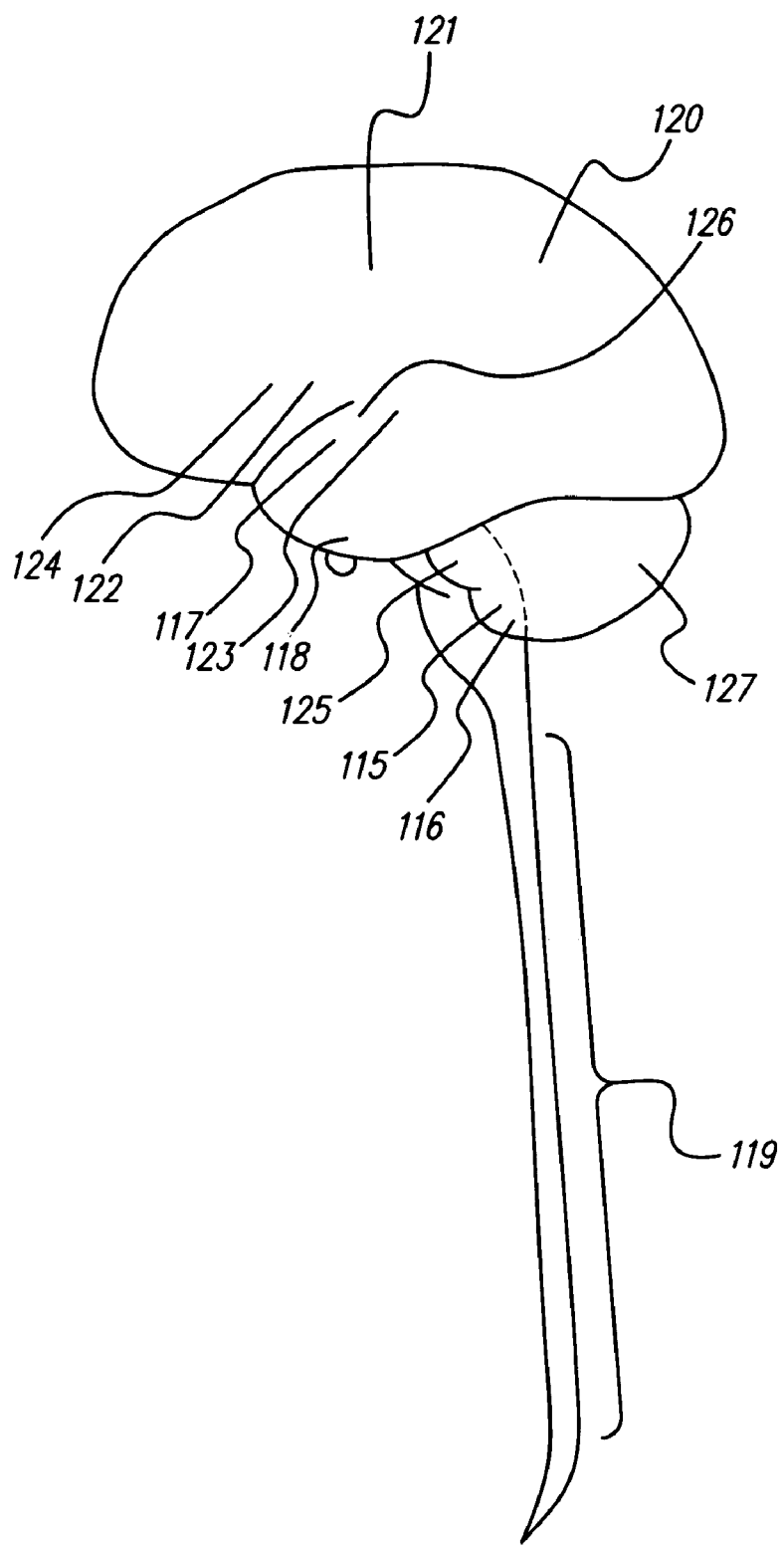
FIG. 1B is a schematic representation of the central nervous system.

FIG. 1B is a schematic of the central nervous system. FIG. 1B shows the approximate locations of the following structures: the cerebellum (127), the nucleus of the solitary tract (115) (located beneath the cerebellum (127)), the dorsal vagal complex (116) (located beneath the cerebellum (127)), the central nucleus of the amygdala (117), the hypothalamus (118) (including the lateral and ventromedial portions of the hypothalamus (118)), the spinal cord (119), the somatosensory cortex (120), the abdominal area of the motor cortex (121), and the pleasure centers in the brain (including the septum pellucidum (122), the ventral striatum (123), the nucleus accumbens (124), the ventral tegmental area (125), and the limbic system (126).

In some embodiments, at least one stimulus is applied with a system control unit (SCU) to one or more stimulation sites within a patient to treat and/or prevent chronic pelvic pain (CPP) and/or the symptoms and pathological consequences of CPP. The terms "stimulus" and "stimulation" will be used interchangeably herein and in the appended claims, unless otherwise specifically denoted, to refer to electrical stimulation, drug stimulation, chemical stimulation, thermal stimulation, electromagnetic stimulation, mechanical stimulation, and/or any other suitable stimulation. The terms "chronic pelvic pain" and "CPP" will be used herein and in the appended claims to refer to any type of chronic pelvic pain and any symptom and/or pathological consequences of chronic pelvic pain including, but not limited to, post hemiorhaphy pain, chronic pain following gynecological procedures, ilio-inguinal neuralgia, endometriosis, pelvic inflammatory disease, aedenomyosis, leiomyomata, adhesions, ovarian cyst(s), ovarian mass(es), endosalpingiosis, cervical stenosis, pelvic relaxation, urethral disorders, diverticulitis, interstitial cystitis, pudendal neuralgia, vulvovestibulitis, and prostatitis.

Furthermore, as used herein and in the appended claims, the term "stimulation site" will be used to refer to a location within a patient to which stimulation may be applied to treat CPP including, but not limited to, one or more of the following: one or more areas of the peripheral nerves, sympathetic nerves, spinal cord, dorsal nerve roots, thalamus and/or cortex. The thalamus and cortex are common destinations in the brain for pain signals. In particular, the stimulation site may include one or more of the following locations: the ilio-inguinal nerve; the inferior hypogastric nerve; the frankenhauser's ganglion; the inferior hypogastric plexus; the superior hypogastric plexus; one or more of the posterior labial nerves; the perineal branch of posterior femoral cutaneous nerve; the perineal nerve; the sympathetic ganglia; the pudendal nerve; one or more of the sacral nerve roots; one or more of the nerves supplying sympathetic control to pelvic region; the pelvic plexus; one or more dorsal columns of the spinal cord; one or more of the dorsal nerve roots supplying the pelvic region including, but not limited to, the cauda equine; the thalamus; the motor cortex; the frontal cortex; the arterial supply to the reproductive organs; the arterial supply to the pelvic floor; the subcutaneous fat; the peritoneal cavity; and intramuscular tissue. Additional or alternative stimulation sites are described in U.S. Pat. No. 6,735,474, U.S. Pat. No. 6,871,099 ("Fully Implantable Microstimulator for Spinal Nerve, Spinal Nerve Root, and/or Spinal Cord Stimulation as a Therapy for Chronic Pain" to Whitehurst et al.), and U.S. Publication 2005/0143789 ("Methods and Systems for Stimulating a Peripheral Nerve to Treat Chronic Pain" to Whitehurst et al.). These patents and documents are all incorporated herein by reference in their respective entireties.

Many of the above listed stimulation sites are relatively easily accessed. An SCU may thus be implanted via injection and/or via endoscopic means adjacent to one or more of these stimulation sites. A more complicated surgical procedure may be required for sufficient access to one or more of these stimulation sites and/or for purposes of fixing the SCU in place.

As mentioned, the stimulus applied to the stimulation site may include electrical stimulation, also known as neuromodulation. Electrical stimulation will be described in more detail below. The stimulus may additionally or alternatively include drug stimulation, also referred to herein as drug infusion. As will be described in more detail below, therapeutic dosages of one or more drugs may be infused into a stimulation site or into a site near the stimulation site to treat chronic pelvic pain. Additionally or alternatively, the stimulus applied to the stimulation site may include any other suitable stimulus such as, but not limited to, chemical stimulation, thermal stimulation, electromagnetic stimulation, and/or mechanical stimulation.

Figure 2:
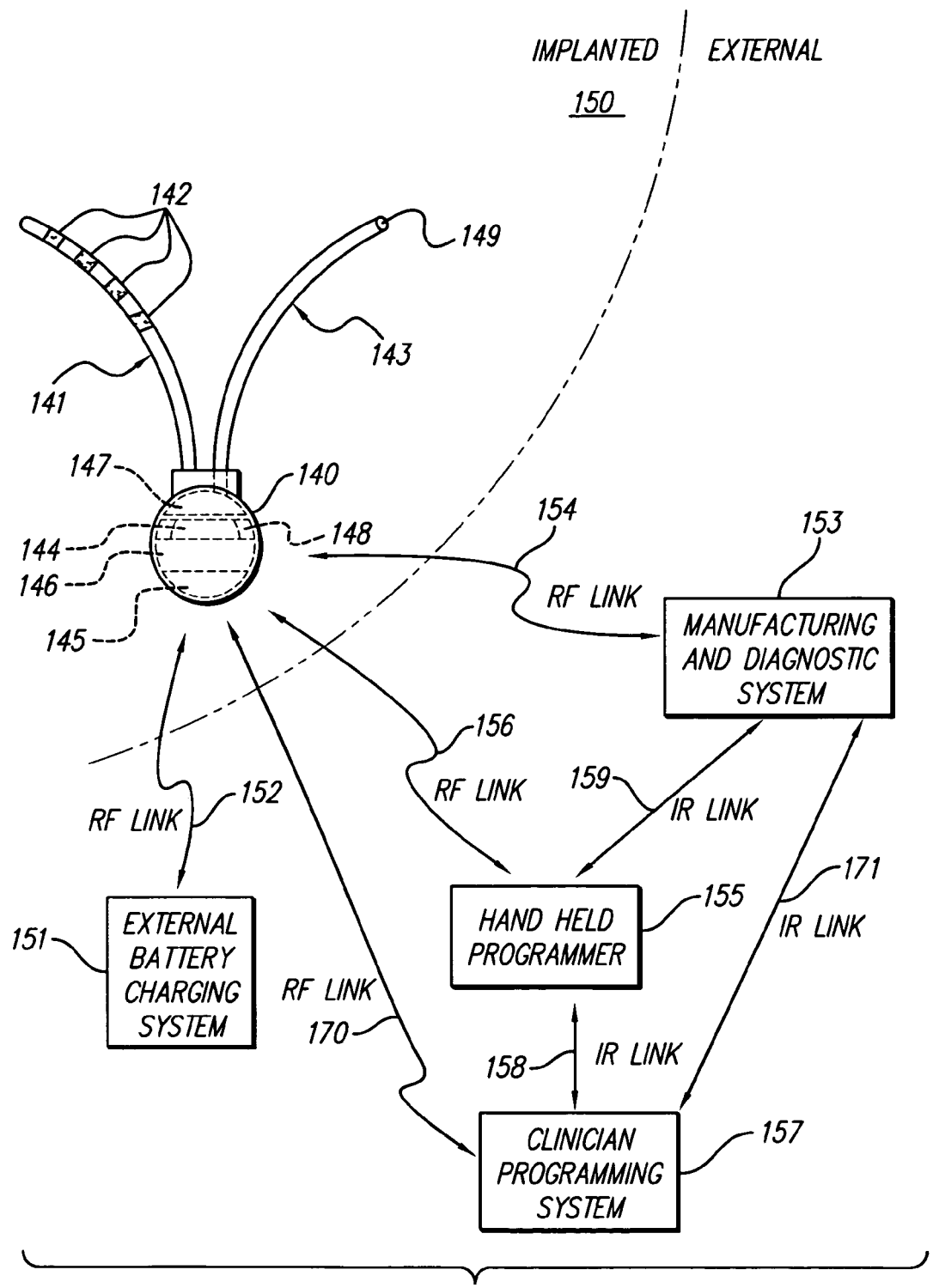
FIG. 2 illustrates an exemplary system control unit (SCU) that may be used to apply stimulation to a stimulation site to treat CPP according to principles described herein.

In some embodiments, the stimulus may be applied to a stimulation site by using one or more implantable system control units (SCUs). FIG. 2 illustrates an exemplary SCU (140) that may be implanted within a patient (150) and used to apply a stimulus to a stimulation site to treat CPP, e.g., an electrical stimulation of the stimulation site, an infusion of one or more drugs into the stimulation site, or both.

The one or more drugs that may be applied to a stimulation site to treat CPP may have an excitatory effect on the stimulation site. Additionally or alternatively, the one or more drugs may have an inhibitory effect on the stimulation site to treat CPP. Exemplary excitatory drugs that may be applied to a stimulation site to treat CPP include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat CPP include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat CPP include at least one or more of the following substances: non-steroidal anti-inflammatory medications (NSAIDS) (e.g., ibuprofen, naproxen, VIOXX); estrogens (e.g., estrone, estradiol, estriol, esters of estradiol, synthetic estrogens such as diethylstilbestrol, quinestrol, chlorotrianisene); progestins (e.g., naturally occurring progesterone, medroxyprogesterone acetate, norethindrone acetate, hydroxyprogesterone acetate, norgestrel, norethindrone); antiestrogens (e.g., clomiphene, tamoxifen); gonadotropin releasing hormone agonist analogues (e.g., leuprolide acetate, nafarelin); androgens (e.g., testosterone, testosterone cypionate, fluoxymesterone, fluoxymesterone, danazol, testolactone); antiandrogens (e.g., cyproterone acetate, flutamide); opioids (e.g., morphine); ziconitide; and/or antidepressants (e.g., serotonin specific reuptake inhibitors and tricyclic antidepressants).

Any of the above listed drugs, alone or in combination, or other drugs developed or shown to treat CPP or its symptoms may be applied to the stimulation site to treat CPP. In some embodiments, the one or more drugs are infused chronically into the stimulation site. Additionally or alternatively, the one or more drugs may be infused acutely into the stimulation site in response to a biological signal or a sensed need for the one or more drugs.

As mentioned, FIG. 2 illustrates an exemplary SCU (140) that may be implanted within a patient (150) and used to apply stimulation to a stimulation site to treat CPP. For example, the SCU (140) may be configured to apply an electrical stimulation current and/or infuse one or more drugs into the stimulation site to treat CPP. The electrical stimulation function of the SCU (140) will be described first, followed by an explanation of the drug delivery function of the SCU (140). It will be understood, however, that a particular SCU (140) may be configured to provide any type of stimulation as best suits a particular patient with CPP.

The exemplary SCU (140) shown in FIG. 2 is configured to provide electrical stimulation to a patient with CPP and includes a lead (141) having a proximal end coupled to the body of the SCU (140). The lead (141) also includes a number of electrodes (142) configured to apply an electrical stimulation current to a stimulation site. In some embodiments, the lead (141) includes anywhere between two and sixteen electrodes (142). However, the lead (141) may include any number of electrodes (142) as best serves a particular application. The electrodes (142) may be arranged as an array, for example, having at least two or at least four collinear electrodes. In some embodiments, the electrodes are alternatively inductively coupled to the SCU (140). The lead (141) may be thin (e.g., less than 3 millimeters in diameter) such that the lead (141) may be positioned near a stimulation site. Alternatively, as will be described in more detail below, the SCU (140) may be leadless.

As illustrated in FIG. 2, the SCU (140) includes a number of components. It will be recognized that the SCU (140) may include additional and/or alternative components as best serves a particular application. A power source (145) is configured to output voltage used to supply the various components within the SCU (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

Alternatively, the SCU (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their entireties. Other battery construction techniques that may be used to make a power source (145) include those shown, e.g., in U.S. Pat. Nos. 6,280,873; 6,458,171, 6,607,843 and 6,605,382, all of which are incorporated herein by reference in their entireties. Recharging can be performed using an external charger.

The SCU (140) may also include a coil (148) configured to receive and/or emit a magnetic field (also referred to as a radio frequency (RF) field) that is used to communicate with or receive power from one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the SCU (140) via one or more RF links (154, 156). It will be recognized that the RF links (152, 154, 156) may be any type of link such as an optical link, a thermal link, or any other energy-coupling link. One or more of these external devices (153, 155, 157) may also be used to control the infusion of one or more drugs by the SCU (140) into a stimulation site to treat CPP.

Additionally, if multiple external devices are used in the treatment of a patient, there may be some communication among those external devices, as well as with the implanted SCU (140). For example, the CPS (157) may communicate with the HHP (155) via an infrared (IR) link (158), with the MDS (153) via an IR link (171), and/or directly with the SCU (140) via an RF link 170. These communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the SCU (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted SCU (140) when in use.

The SCU (140) may also include electrical circuitry (144) configured to produce electrical stimulation pulses that are delivered to the stimulation site via the electrodes (142). In some embodiments, the SCU (140) may be configured to produce monopolar stimulation. The SCU (140) may alternatively or additionally be configured to produce bipolar or tripolar stimulation. Monopolar electrical stimulation is achieved, for example, using the stimulator case as an indifferent electrode. Bipolar or tripolar electrical stimulation is achieved, for example, using one or more of the electrodes of the electrode array as an indifferent electrode. The electrical circuitry (144) may include one or more processors configured to decode stimulation parameters and generate the stimulation pulses. In some embodiments, the SCU (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The SCU (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the SCU (140) to adjust the stimulation parameters such that the stimulation applied by the SCU (140) is safe and efficacious for treatment of a particular patient with CPP. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused into the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on neural or other tissue. Thus, in some embodiments, the stimulation parameters may be adjusted by the patient, a clinician, or other user of the SCU (140) as best serves a particular stimulation site. The stimulation parameters may also be automatically adjusted by the SCU (140), as will be described below. For example, the amplitude of the stimulus current applied to a stimulation site may be adjusted to have a relatively low value to target a nerve having relatively large diameter fibers. The SCU (140) may also increase excitement of a stimulation site by applying a stimulation current having a relatively low frequency to the stimulation site (e.g., less than 100 Hz). The SCU (140) may also decrease excitement of a stimulation site by applying a relatively high frequency to the stimulation site (e.g., greater than 100 Hz). The SCU (140) may also be programmed to apply the stimulation current to a stimulation site intermittently or continuously.

Additionally, the exemplary SCU (140) shown in FIG. 2 is configured to provide drug stimulation to a CPP patient. For this purpose, the SCU (140) includes a pump (147). The pump (147) is configured to store and dispense one or more drugs, for example, through a catheter (143). The catheter (143) is coupled at a proximal end to the SCU (140) and may have an infusion outlet (149) for infusing dosages of one or more drugs into a stimulation site. In some embodiments, the SCU (140) may include multiple catheters (143) and/or pumps (147) for storing and infusing dosages of the one or more drugs into the stimulation site or into multiple stimulation sites.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

Figure 3:
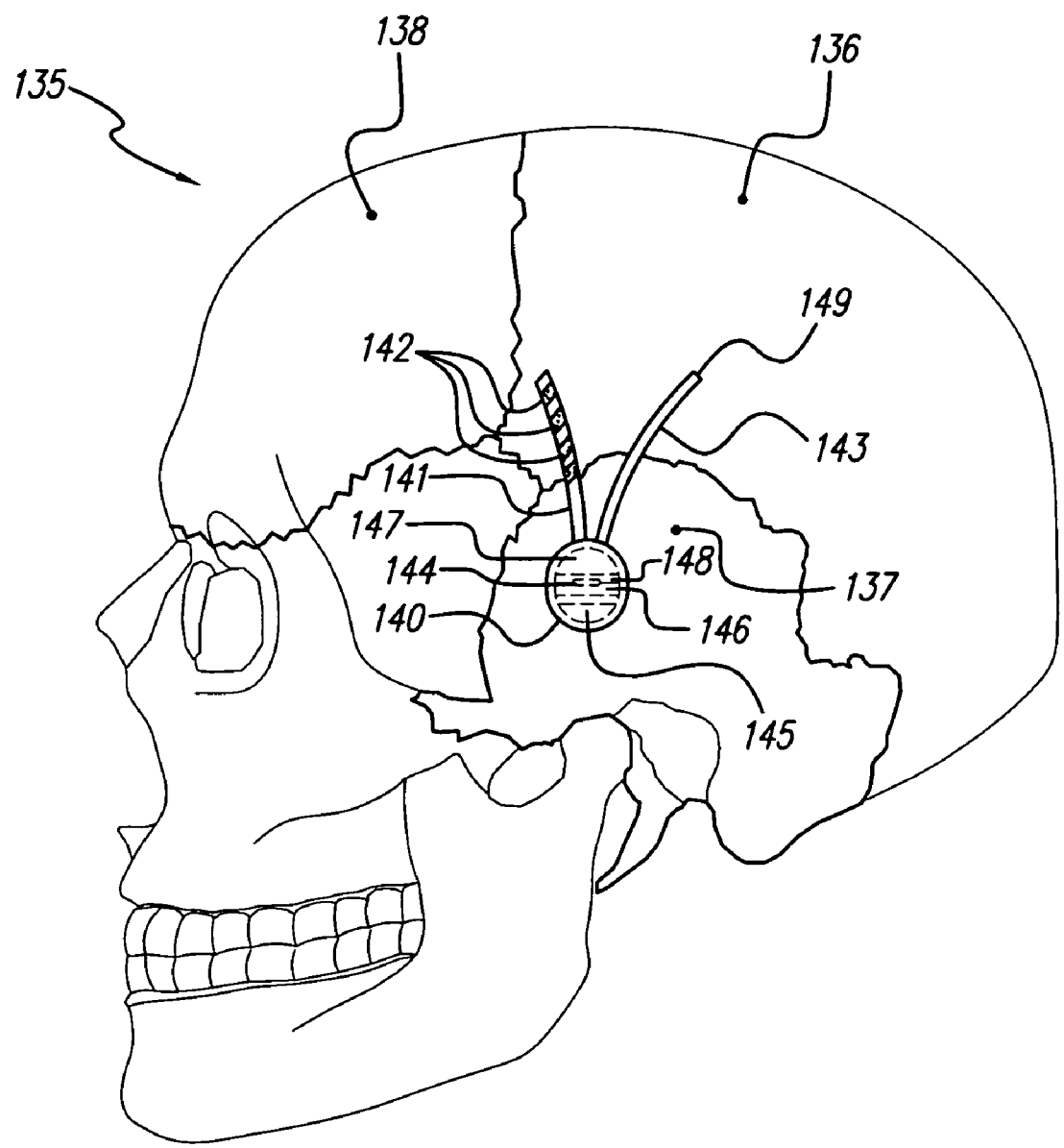
FIG. 3 shows an SCU implanted in the skull relatively close to a stimulation site within the brain according to principles described herein.

The SCU (140) of FIG. 2 may be implanted within the patient (150) using any suitable surgical procedure such as, but not limited to, injection, small incision, open placement, laparoscopy, or endoscopy. In some instances, the SCU (140) may be implanted at a site that is relatively close to a stimulation site with the lead (141) and/or the catheter (143) being routed to the stimulation site. For example, FIG. 3 shows an SCU (140) that has been implanted beneath the scalp of a patient. The SCU (140) may be implanted in a surgically-created shallow depression or opening in the skull (135). For instance, the depression may be made in the parietal bone (136), temporal bone (137), frontal bone (138), or any other bone within the skull (135) as best serves a particular application. The SCU (140) may conform to the profile of surrounding tissue(s) and/or bone(s), thereby minimizing the pressure applied to the skin or scalp. In some embodiments, the lead (141) and/or catheter (143) run subcutaneously to an opening in the skull (135) and pass through the opening into or onto a stimulation site in the brain, cervical spinal cord, thalamus, cortex, or any other location within the patient. The SCU (140) itself may alternatively be coupled directly to the stimulation site.

The SCU (140) of FIG. 2 is illustrative of many types of SCUs that may be used to treat CPP. For example, the SCU (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus to a stimulation site within a patient. Exemplary IPGs suitable for use as described herein include, but are not necessarily limited to, those disclosed in U.S. Pat. Nos. 6,381,496, 6,553, 263; and 6,760,626. Exemplary spinal cord stimulators suitable for use as described herein include, but are not necessarily limited to, those disclosed in U.S. Pat. Nos. 5,501,703; 6,487,446; and 6,516,227. Exemplary cochlear implants suitable for use as described herein include, but are not necessarily limited to, those disclosed in U.S. Pat. Nos. 6,219,580; 6,272,382; and 6,308,101. Exemplary deep brain stimulators suitable for use as described herein include, but are not necessarily limited to, those disclosed in U.S. Pat. Nos. 5,938, 688; 6,016,449; and 6,539,263. All of these listed patents are incorporated herein by reference in their respective entireties.

Alternatively, the SCU (140) include an implantable microstimulator, such as a BION® microstimulator (Advanced Bionics® Corporation, Valencia, Calif.). Various details associated with the manufacture, operation, and use of BION implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 4:
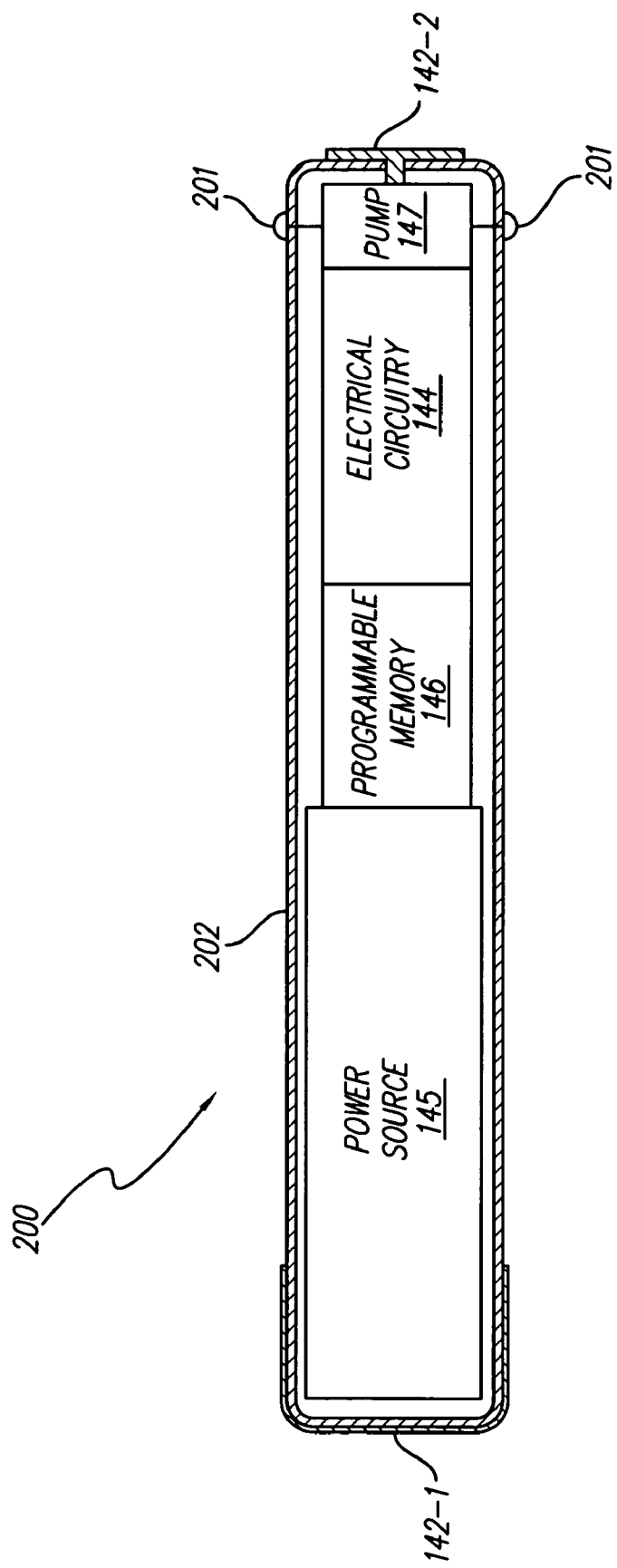
FIG. 4 illustrates an exemplary BION microstimulator that may be used as the SCU according to principles described herein.

FIG. 4 illustrates an exemplary BION microstimulator (200) that may be used as the SCU (140; FIG. 2) described herein. Other configurations of the microstimulator (200) are possible, as shown in the above-referenced patents and as described further below.

As shown in FIG. 4, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired stimulation site, the surrounding area, and the method of implementation. In some embodiments, the capsule (202) is substantially equal to or less than three cubic centimeters.

In some embodiments, the microstimulator (200) may include two or more leadless electrodes (142). Either or both of the electrodes (142) may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, polymers, metal, or any other material that provides a hermetic package that will exclude water vapor but permit passage of electromagnetic fields used to transmit data and/or power. The electrodes (142) may be made of a conducting ceramic, conducting polymer, and/or a noble or refractory metal, such as gold, silver, platinum, iridium, tantalum, titanium, titanium nitride, niobium or their alloys that, e.g., minimize corrosion, electrolysis, and damage the surrounding tissues.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques. As previously mentioned, the microstimulator (200) may be coupled directly to a stimulation site.

FIG. 4 shows that the microstimulator (200) may also include one or more infusion outlets (201). The infusion outlets (201) facilitate the infusion of one or more drugs into a stimulation site to treat a particular medical condition. The infusion outlets (201) may dispense one or more drugs, chemicals, or other substances directly to the stimulation site. Alternatively, as will be described in more detail below, catheters may be coupled to the infusion outlets (201) to deliver the drug therapy to a stimulation site some distance from the body of the microstimulator (200). The stimulator (200) of FIG. 4 also includes electrodes (142-1 and 142-2) at either end of the capsule (202). One of the electrodes (142) may be designated as a stimulating electrode to be placed close to the stimulation site and one of the electrodes (142) may be designated as an indifferent electrode used to complete a stimulation circuit.

Figure 5:
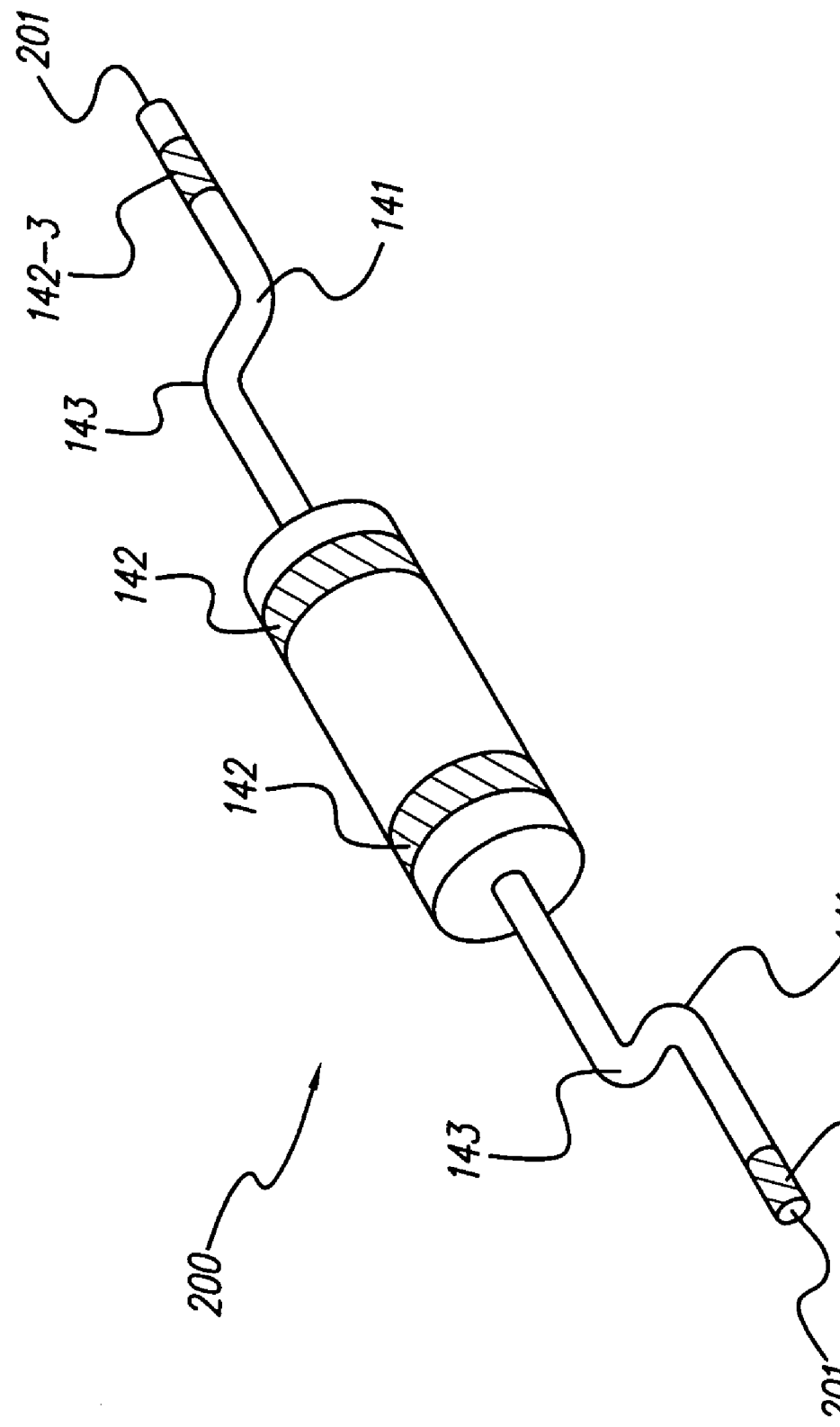
FIG. 5 shows one or more catheters coupled to the microstimulator according to principles described herein.

FIG. 5 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the ends of catheters (143). Thus, in the example of FIG. 5, a drug therapy is expelled by the pump (147, FIG. 4) from an infusion outlet (201, FIG. 4) in the casing (202, FIG. 4) of the microstimulator (200), through the catheter (143), out an infusion outlet (201) at the end of the catheter (143) to the stimulation site within the patient. As shown in FIG. 5, the catheters (143) may also serve as leads (141) having one or more electrodes (142-3) disposed thereon. Thus, the catheters (143) and leads (141) of FIG. 5 permit infused drugs and/or electrical stimulation to be directed to a stimulation site while allowing most elements of the microstimulator (200) to be located in a more surgically convenient site. The example of FIG. 5 may also include leadless electrodes (142) disposed on the housing of the microstimulator (200), in the same manner described above.

Figure 6:
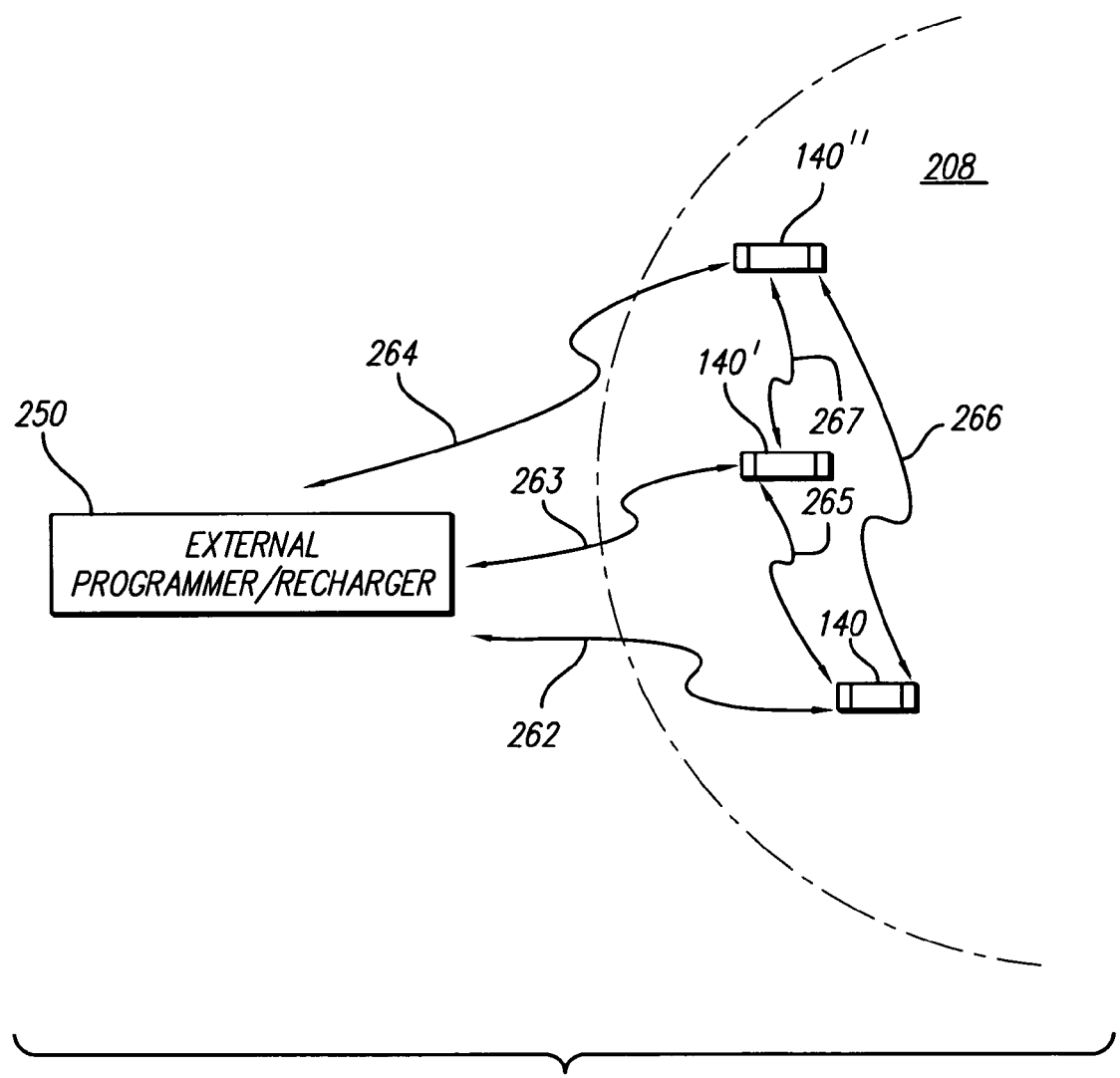
FIG. 6 depicts a number of SCUs configured to communicate with each other and/or with one or more external devices according to principles described herein.

Returning to FIG. 2, the SCU (140) may be configured to operate independently. Alternatively, as shown in FIG. 6 and described in more detail below, the SCU (140) may be configured to operate in a coordinated manner with one or more additional SCUs, other implanted devices, or other devices external to the patient's body. For instance, a first SCU may control or operate under the control of a second SCU, other implanted device, or other device external to the patient's body. The SCU (140) may be configured to communicate with other implanted SCUs, other implanted devices, or other devices external to the patient's body via an RF link, an ultrasonic link, an optical link, or any other type of communication link. For example, the SCU (140) may be configured to communicate with an external remote control that is capable of sending commands and/or data to the SCU (140) and that is configured to receive commands and/or data from the SCU (140).

In order to determine the amount and/or type(s) of stimulating drug(s) and/or the strength and/or duration of electrical stimulation required to most effectively treat CPP, various indicators of CPP and/or a patient's response to treatment may be sensed or measured. These indicators include, but are not limited to, electrical activity of the brain (e.g., EEG); neurotransmitter levels; hormone levels; metabolic activity in the brain; blood flow rate in one or more tissues within the body; temperature in superficial tissues (e.g., skin in perineum); presence of blood and/or other products of endometrial shedding outside of the uterus (e.g., in the peritoneal cavity); and/or medication levels within the patient. In some embodiments, the SCU (140) may be configured to change the stimulation parameters in a closed loop manner in response to these measurements. The SCU (140) may be configured to perform the measurements. Alternatively, other sensing devices may be configured to perform the measurements and transmit the measured values to the SCU (140). Exemplary sensing devices include, but are not limited to, chemical sensors, electrodes, optical sensors, mechanical (e.g., motion, pressure) sensors, and temperature sensors.

Thus, one or more external appliances may be provided to interact with the SCU (140), and may be used to accomplish at least one or more of the following functions:

Function 1: If necessary, transmit electrical power to the SCU (140) in order to power the SCU (140) and/or recharge the power source (145).

Function 2: Transmit data to the SCU (140) in order to change the stimulation parameters used by the SCU (140).

Function 3: Receive data indicating the state of the SCU (140) (e.g., battery level, drug level, stimulation parameters, etc.).

Additional functions may include adjusting the stimulation parameters based on information sensed by the SCU (140) or by other sensing devices.

By way of example, an exemplary method of treating a patient with CPP may be carried out according to the following sequence of procedures. The steps listed below may be modified, reordered, and/or added to as best serves a particular application.

1. An SCU (140) is implanted so that its electrodes (142) and/or infusion outlet (149) are coupled to or located near a stimulation site. If the SCU (140) is a microstimulator, such as the BION microstimulator (200; FIG. 4), the microstimulator itself may be coupled to the stimulation site.

2. The SCU (140) is programmed to apply at least one stimulus to the stimulation site. The stimulus may include electrical stimulation, drug stimulation, chemical stimulation, thermal stimulation, electromagnetic stimulation, mechanical stimulation, and/or any other suitable stimulation.

3. When the patient desires to invoke stimulation, the patient sends a command to the SCU (140) (e.g., via a remote control) such that the SCU (140) delivers the prescribed stimulation. The SCU (140) may be alternatively or additionally configured to automatically apply the stimulation in response to sensed indicators of CPP.

4. To cease stimulation, the patient may turn off the SCU (140) (e.g., via a remote control).

5. Periodically, the power source (145) of the SCU (140) is recharged, if necessary, in accordance with Function 1 described above.

In other examples, the treatment administered by the SCU (140), i.e., drug therapy and/or electrical stimulation, may be automatic and not controlled or invoked by the patient.

For the treatment of different patients with CPP, it may be desirable to modify or adjust the algorithmic functions performed by the implanted and/or external components, as well as the surgical approaches. For example, in some situations, it may be desirable to employ more than one SCU (140), each of which could be separately controlled by means of a digital address. Multiple channels and/or multiple patterns of stimulation may thereby be used to deal with multiple symptoms of CPP.

For instance, as shown in the example of FIG. 6, a first SCU (140) implanted beneath the skin of the patient (208) provides a stimulus to a first location; a second SCU (140') provides a stimulus to a second location; and a third SCU (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. SCU (140), may control or operate under the control of another implanted device(s), e.g. SCU (140') and/or SCU (140"). Control lines (262-267) have been drawn in FIG. 6 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple SCUs (140) operating in a coordinated manner, the first and second SCUs (140, 140') of FIG. 6 may be configured to sense various indicators of CPP and transmit the measured information to the third SCU (140"). The third SCU (140") may then use the measured information to adjust its stimulation parameters and apply stimulation to a stimulation site accordingly. The various implanted SCUs may, in any combination, sense indicators of CPP, communicate or receive data on such indicators, and adjust stimulation parameters accordingly.

Alternatively, the external device (250) or other external devices communicating with the external device may be configured to sense various indicators of a patient's condition. The sensed indicators can then be transmitted to the external device (250) for relay to one or more of the implanted SCUs or may be transmitted directly to one or more of the implanted SCUs. In either case, the SCU, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the SCUs to adjust stimulation parameters accordingly.

By way of example, a number of exemplary methods of implanting a lead (141) and/or catheter (143) of an SCU (140) at or near a stimulation site to treat a patient with CPP may be carried out according to the following sequence of procedures. In the following exemplary methods, the stimulation site is the pudendal nerve for illustrative purposes. It will be understood that the exemplary methods described below may be modified to implant the SCU (140) at any of the stimulation sites listed above or any other stimulation sites discovered to be effective in treating CPP. It will also be understood that the SCU (140) described in connection with the exemplary methods described below may be an IPG, SCS, cochlear implant, deep brain stimulator, drug pump, micro-drug pump, or any other type of implantable stimulator as described above. Exemplary methods of implanting an SCS, for example, are described in U.S. Pat. Nos. 5,501,703; 6,487, 446; and 6,516,227. Exemplary methods of implanting a deep brain stimulator, for example, are described in U.S. Pat. Nos. 5,938,688; 6,016,449; and 6,539,263. All of these listed patents are incorporated herein by reference in their respective entireties.

The steps listed below may be modified, reordered, and/or added to as best serves a particular application.

Figure 7A:
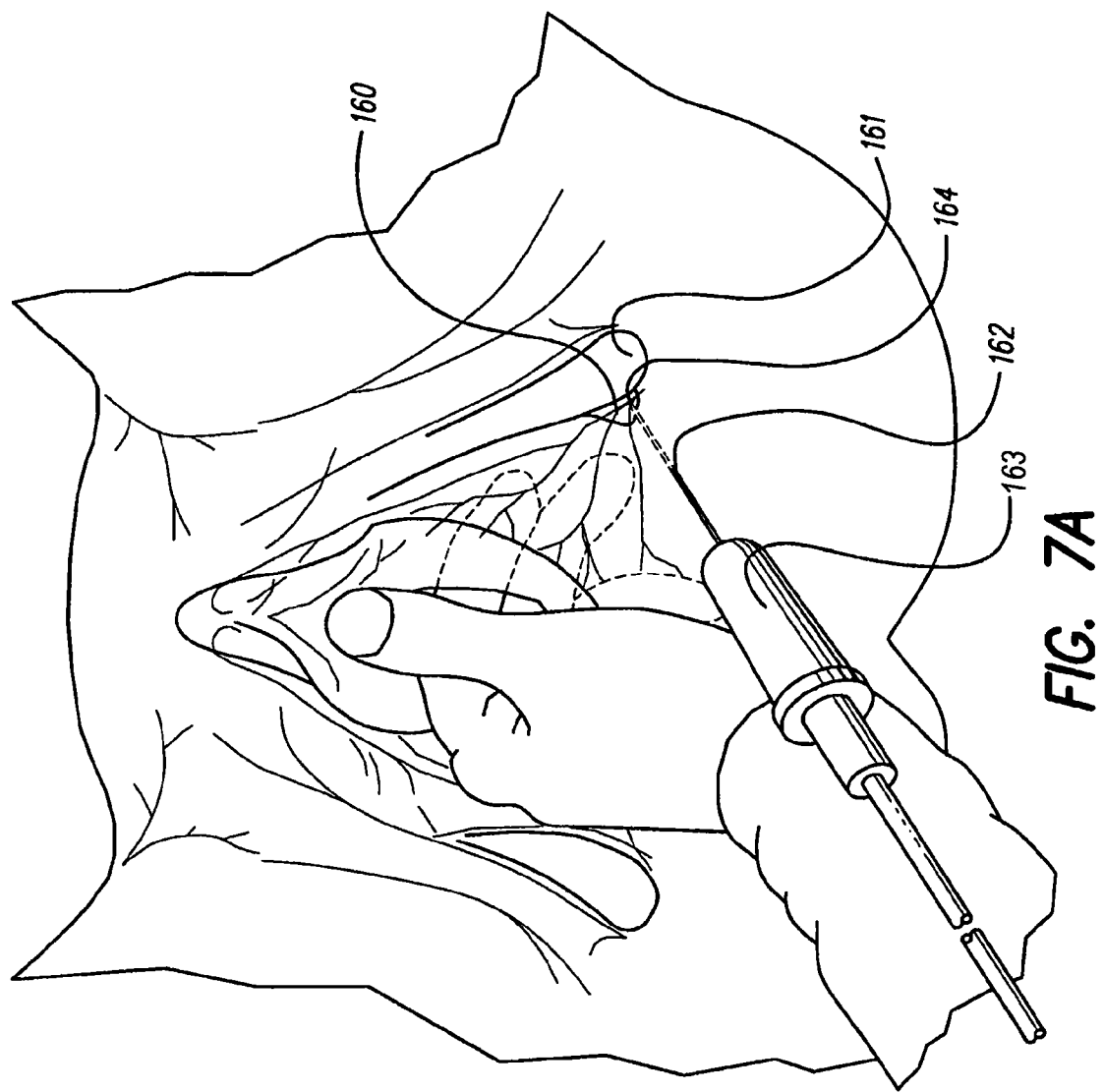
FIG. 7A depicts an exemplary method of advancing an insertion tool toward the pudendal nerve according to principles described herein.
Figure 7B:
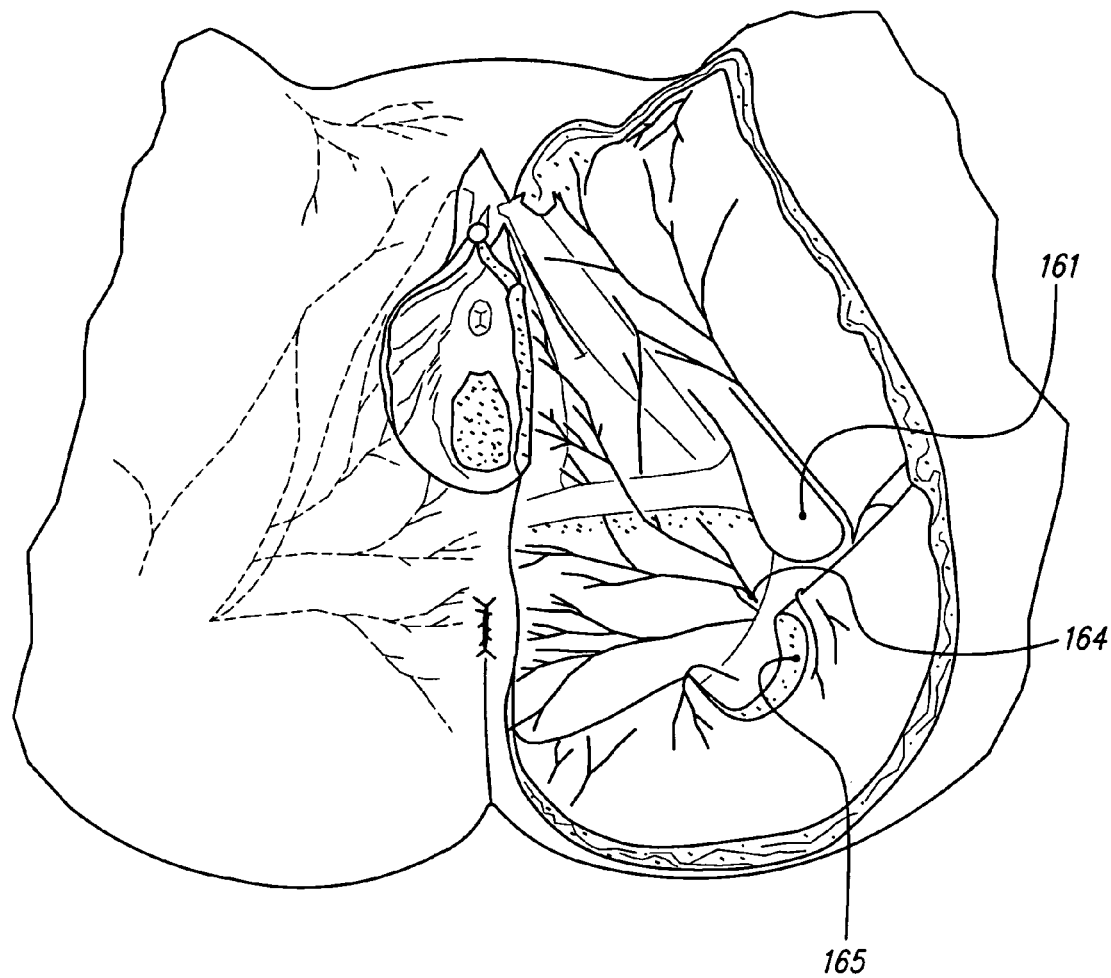
FIG. 7B is a partial dissection depicting various bones, nerves, muscles, and other tissues of the female perineum.

A first exemplary method of implanting a lead and/or catheter ("lead/catheter") of an SCU (140) at or near the pudendal nerve (164) to treat a patient with CPP is referred to as a perineal approach or method. As seen in FIG. 7A, the ischial spine (160) may be used as a landmark for locating the pudendal nerve (164), as may the ischial tuberosity (161) (visible in FIGS. 7A, 7B, and 7C). The perineal approach for a female patient may include one or more of the following steps.

Figure 7C:
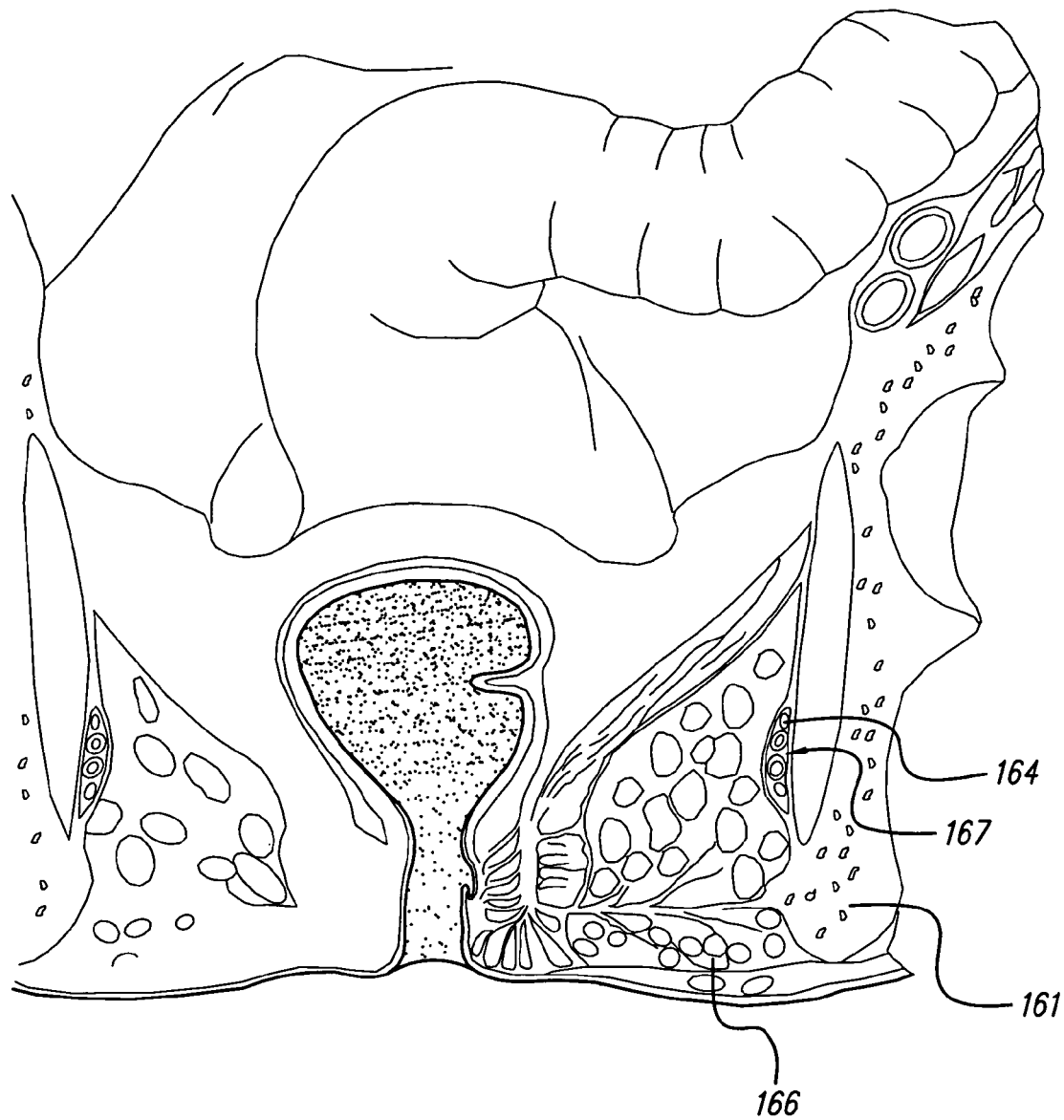
FIG. 7C is a dissection depicting various bones, nerves, muscles, vessels, and other tissues of the ischioanal fossa.

1. Locate the ischial tuberosity (IT) (161) through the skin. As best seen in FIG. 7C, a portion of the IT (161) lies close to the surface of the skin.

2. Mark the skin 1-5 mm medial from the IT (161). This defines the site (162) for inserting a tool (163) for lead/catheter placement.

3. As depicted in FIG. 7A, locate the ischial spine (IS) (160) by inserting one or two fingers into the vagina (or anus) and palpating laterally (a procedure known in the medical arts). The pudendal nerve (164) in the pudendal canal (167) (FIG. 7C) lies adjacent to the IS (160).

4. Guide the insertion tool (163) toward the IS (160). Use finger pressure against the vaginal (or anal) wall to track insertion of the tool (163) from the marked insertion site (162) toward the IS (160).

5. Using techniques known in the art, optionally perform test stimulation to confirm proper lead and/or catheter location, to confirm response, and/or to determine preliminary stimulator settings. (This test stimulation may be referred to as an acute trial, an operating room trial, or a procedure room trial, for example, and may last for any amount of time.) For instance, the insertion tool may include a tip electrode, electrodes of a lead inserted through the tool, or a test catheter configured to deliver drugs or electrical stimulation on a test basis while analyzing patient response. Alternatively, a monopolar needle electrode or the like may be used. Response(s) may include patient report of sensation, vaginal EMG, urethral sphincter PeNTML and/or anal sphincter PNTML, or other responses known in the art.

6. Once the desired stimulation site has been located, the next step is to deposit or secure the lead/catheter at the stimulation site. Depending on the type of tool and lead/catheter used, this step may include pushing the lead/catheter out of a cannula and/or expelling a biocompatible adhesive to help secure the lead/catheter to surrounding tissue. Additionally or alternatively, the lead/catheter may be secured within the patient with self-securing barbs, anchors, sutures, or the like. The lead/catheter may be secured in any of a number of different locations within a patient including, but not limited to, subcutaneous muscle (165) (FIG. 7B), fascia (166) (FIG. 7C), or other location at the insertion site or along the lead/catheter path.

7. Once the lead/catheter is secured at the stimulation site, test stimulation may be optionally performed to confirm correct location of the lead/catheter. If the lead/catheter is not properly positioned, any of the previous steps may be repeated to reposition the lead/catheter.

8. If the tool (163) is not removed while securing the lead/catheter, remove the tool (163).

An alternative method of implanting a lead/catheter of an SCU (140) at or near the pudendal nerve (164) and/or its branches to treat a patient with CPP is known as the vaginal approach. The vaginal approach may include one or more of the following steps.

1. Grossly locate the pudendal nerve (164) in the pudendal canal by inserting one or two fingers into the vagina and palpating laterally to locate the IS (160).

2. Insert a speculum into the vagina.

3. With the speculum inserted, locate pudendal nerve (164) in the pudendal canal by inserting one or two fingers into the vagina and palpating laterally to locate the IS (160).

4. Guide the insertion tool (163) through the vaginal wall toward the IS (160).

5. Using techniques known in the art, optionally perform test stimulation to confirm proper lead and/or catheter location, to confirm response, and/or to determine preliminary stimulator settings, as described above.

6. Once at the desired location, deposit the lead/catheter, as described above. The lead/catheter may be secured in place as described above or by anchoring the lead/catheter to tissue exposed through an incision made in the vaginal wall.

7. Once the lead/catheter is deposited and/or anchored, again optionally perform test stimulation to confirm that the lead/catheter has not shifted out of position. If necessary, repeat any of the above mentioned steps to reposition the lead/catheter.

8. If the speculum and tool (163) are not removed while securing the lead/catheter, remove the speculum and tool (163).

Once the lead and/or catheter is in place, one or more tunnels may be made to an SCU implantation site. The tunnels may additionally or alternatively be made to a percutaneous trial exit site if a percutaneous trial is to be conducted prior to permanent implantation of the SCU (140). To tunnel to a percutaneous trial exit site, one or more of the following steps may be used:

1. Locate and mark the percutaneous trial exit site. The trial exit site may be contralateral and symmetrical to the planned SCU implant site, for example. However, it will be recognized that various locations may be used as the trial exit site.

2. Run a tunneling tool from the lead/catheter implantation site to the marked percutaneous trial exit site or run a tunneling tool from the marked percutaneous trial exit site to the lead/catheter implantation site. In either case, the tunnel may be subcutaneously located. In some alternative embodiments, the tunnel(s) may run deeper within the body of the patient. If necessary, an incision(s) may be made to tunnel in sections, as may be needed if a lead/catheter extension(s) is used.

3. Pull lead(s)/catheter(s)/extension(s) through the tunnel or tunnel sections. As appropriate, connect any extension(s) to the implanted catheter/lead. The lead(s)/catheter(s)/extension(s) may be pulled either from the lead/catheter implantation site or from the percutaneous trial exit site. For trial stimulation, a percutaneous extension may be pulled from the exit site to the lead/catheter implantation site and connected to the implanted catheter/lead. When trial stimulation is complete, the connector may be cut off from the percutaneous extension so that the extension may be pulled back through the percutaneous exit site to reduce infection risk. The proximal end of the lead(s)/catheter(s)/extension(s) (which attaches to the trial SCU) should extend from the marked percutaneous trial exit site.

4. Attach the proximal end of the lead(s)/catheter(s)/extension(s) to the trial stimulator.

5. Optionally perform test stimulation to confirm proper lead and/or catheter location, confirm proper trial stimulator function, and/or to determine preliminary settings for the SCU (140) that is to be permanently implanted.

6. Surgically close the skin at the lead/catheter implantation site and around the lead/catheter/extension at the percutaneous trial exit site, using techniques known in the art.

To tunnel to an SCU implantation site and implant the SCU (140), one or more of the following steps may be used:

1. Locate and mark the SCU implantation site.

2. Run a tunneling tool(s) from the lead/catheter implantation site to the marked SCU implantation site or make an incision at the SCU implantation site and run a tunneling tool(s) from the incision to the lead/catheter implantation site. In either case, the tunnel(s) may be subcutaneously located. In some alternative embodiments, the tunnel(s) may run deeper within the body of the patient. If necessary, an additional incision(s) may be made to tunnel in sections, as may be needed if a lead/catheter extension(s) is used.

3. Using techniques known in the art, pull lead(s)/catheter(s)/extension(s) through the tunnel or tunnel sections. As appropriate, connect any extension(s) to the implanted catheter/lead. The lead(s)/catheter(s)/extension(s) may be pulled either toward the lead/catheter implantation site or toward the SCU implantation site until the proximal end of the lead(s)/catheter(s)/extension(s) (which attaches to the SCU (140)) extends from the marked SCU implantation site.

4. Attach the proximal end of the lead(s)/catheter(s)/extension(s) to the SCU (140).

5. Optionally perform test stimulation to confirm proper lead and/or catheter location, proper SCU function, and/or to determine preliminary SCU settings.

6. Implant the SCU (140) using any suitable method of implantation.

7. Surgically close the skin at the SCU implantation site and at the lead/catheter implantation site.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with chronic pelvic pain, said method comprising:
    implanting a system control unit at least partially within said patient;
    implanting one or more electrodes at a stimulation site within said patient, wherein said system control unit is coupled to the one or more electrodes;
    configuring one or more stimulation parameters to treat chronic pelvic pain;
    programming said system control unit with said one or more stimulation parameters;
    generating a stimulus configured to treat said chronic pelvic pain with said system control unit in accordance with said one or more stimulation parameters; and
    applying said stimulus to the stimulation site within said patient using said electrodes;
    wherein said stimulation site comprises at least one or more of a frankenhauser's ganglion, a cauda equina, a thalamus, a motor cortex, a frontal cortex, an arterial supply to a reproductive organ, and an arterial supply to a pelvic floor.

2. The method of claim 1, wherein said stimulus further comprises stimulation via one or more drugs delivered to said stimulation site.

3. The method of claim 1, wherein said stimulus comprises a stimulation current delivered to said stimulation site and a stimulation via one or more drugs delivered to said stimulation site.

4. The method of claim 1, further comprising sensing at least one indicator related to said chronic pelvic pain and using said at least one sensed indicator to adjust one or more of said stimulation parameters.

5. The method of claim 4, wherein said at least one indicator comprises at least one or more of an electrical activity of a brain, a neurotransmitter level, a hormone level, and a medication level.

6. The method of claim 1, wherein said system control unit comprises a microstimulator.

7. The method of claim 1, wherein said one or more electrodes are disposed on an outer surface of said system control.

8. The method of claim 1, wherein the stimulation site comprises or the frankenhauser's ganglion.

9. The method of claim 1, wherein the stimulation site comprises the cauda equina.

10. The method of claim 1, wherein the stimulation site comprises the thalamus.

11. The method of claim 1, wherein the stimulation site comprises the motor cortex.

12. The method of claim 1, wherein the stimulation site comprises the frontal cortex.

13. A method of treating a patient with chronic pelvic pain, said method comprising:

implanting a system control unit within said patient;

implanting one or more electrodes at a stimulation site within said patient, wherein said system control unit is coupled to the one or more electrodes;

configuring one or more stimulation parameters to treat chronic pelvic pain;

programming said system control unit with said one or more stimulation parameters;

generating a stimulation current configured to treat said chronic pelvic pain with said system control unit in accordance with said one or more stimulation parameters; and applying said stimulation current to the stimulation site within said patient using said one or more electrodes;

wherein said stimulation site comprises at least one or more of a frankenhauser's ganglion, a cauda equina, a thalamus, a motor cortex, a frontal cortex, an arterial supply to a reproductive organ, and an arterial supply to a pelvic floor.

14. The method of claim 13, further comprising sensing at least one indicator related to said chronic pelvic pain and using said at least one sensed indicator to adjust one or more of said stimulation parameters.

* * * * *